United States Patent [19]
Ideno et al.

[11] Patent Number: 5,989,593
[45] Date of Patent: Nov. 23, 1999

[54] METHOD FOR PRODUCING ANTITHROMBIN-III, METHOD FOR PURIFYING IT, AND PREPARATION CONTAINING IT

[75] Inventors: Shouji Ideno; Katsuhiro Uriyu; Yahiro Uemura, all of Osaka, Japan

[73] Assignee: Yoshitomi Pharmaceutical Industries, Ltd., Osaka, Japan

[21] Appl. No.: 08/974,191

[22] Filed: Nov. 19, 1997

[30] Foreign Application Priority Data

Nov. 20, 1996 [JP] Japan ................................... 8-309281
Jun. 4, 1997 [JP] Japan ................................... 9-163426

[51] Int. Cl.$^6$ .......................... A61K 35/14; A61K 38/16
[52] U.S. Cl. ................................. 424/529; 514/8
[58] Field of Search ................................ 424/529; 514/8

[56] References Cited

U.S. PATENT DOCUMENTS 3,842,061  10/1974  Anderson et al. .................. 260/112 B
4,340,589   7/1982  Uemura et al. ........................ 424/101

FOREIGN PATENT DOCUMENTS 29 16 711  11/1980  Denmark .
0 653 212 A1  5/1995  European Pat. Off. .

OTHER PUBLICATIONS

J. Porath et al. "Metal Chelate Affinity Chromatography, a New Approach to Protein Fractionation" *Nature*, vol. 258, Dec. 18, 1975, p. 598/599 XP002059246.

Newton et al. J. Biol. Chem., 269 (43), 26739–45 (Abstract), 1944.

*Primary Examiner*—Raymond Henley, III
*Attorney, Agent, or Firm*—Sughrue, Mion, Zinn, Macpeak & Seas, PLLC

[57] ABSTRACT

A method for producing antithrombin-III from an antithrombin-III-containing aqueous solution, comprising at least one of the following steps (a) and (b): (a) heating the antithrombin-III-containing aqueous solution in the presence of a stabilizing agent so that 85% or more of the activity of antithrombin-III before the heating is maintained after the heating, and that the ratio of an antithrombin-III monomer after the heating is maintained at 95% or more; and (b) treating the antithrombin-III-containing aqueous solution with a metal chelate resin and recovering a purified antithrombin-III.

19 Claims, 4 Drawing Sheets

BEFORE CHROMATOGRAPHY

AFTER CHROMATOGRAPHY

BEFORE CHROMATOGRAPHY

AFTER CHROMATOGRAPHY

5,989,593

METHOD FOR PRODUCING ANTITHROMBIN-III, METHOD FOR PURIFYING IT, AND PREPARATION CONTAINING IT

FIELD OF THE INVENTION

The present invention relates to a method for producing antithrombin-III, a method for purifying it, and a preparation containing it. More particularly, it relates to a method for producing and purifying antithrombin-III which is used for treating various diseases caused by, for example, reduced availability of antithrombin-III in the body and a preparation containing the thus produced and purified antithrombin-III.

BACKGROUND OF THE INVENTION

Antithrombin-III (hereinafter referred to as "AT-III") is a glycoprotein belonging to $\alpha_2$ globulin, and is present in blood plasma. AT-III has a molecular weight of 65,000 to 68,000 and a protease inhibition activity. AT-III strongly inhibits coagulation activity of thrombin.

Also, AT-III possesses inhibition activities against not only thrombin but also against other coagulation factors, such as activated factor X and activated factor IX. Furthermore, it has been reported that AT-III possesses inhibition activities against plasmin and trypsin.

These inhibition activities are generally more rapid in the coexistence of heparin.

AT-III having such activities has been used for treating abnormal hypercoaglulability, specifically disseminated intravascular coagulation (DIC) and various other diseases caused by the decreased availability of AT-III.

Moreover, AT-III has an affinity for heparin, and a number of purification methods have been reported in which immobilized heparin is used based on such affinity property (e.g., JP-A-63-23896; the term "JP-A" as used herein means an "unexamined published Japanese patent application").

In addition, since AT-III is a protein which is present in blood plasma, inactivation of virus potentially contained therein is required when it is used as a therapeutic preparation.

Among these virus inactivation treatments, a liquid state heat treatment at 60° C. for 10 hours is known as a specific example. However, it has been reported that AT-III is stable at pH 6 to 8, but 80% of the activity is lost by a heat treatment at 56° C. for 6 hours (*J. Biol. Chem.*, 246:3694 (1971)). On the other hand, there are many reports stating that the activity of AT-III is stably maintained when AT-III is subjected to a liquid state heat treatment at 60° C. for 10 hours in the presence of 14.7 w/v % sodium citrate (*Thrombosis Research*, 22:233 (1981) and *J. Biol. Chem.*, 256:12140 (1981)). However, when AT-III is heated in the liquid state even in the presence of 0.35 to 1.5 M (10.29 to 44.12 w/v %) sodium citrate, denaturation of AT-III is observed by immunoelectrophoresis analysis (*Vox Sang*, 48:325 (1985)).

Since such inactivation treatment of viruses also generates denatured protein such as inactivated AT-III, polymerized protein or the like as discussed above, methods have been reported for elimination of such impurities, for example, by carrying out the immobilized heparin treatment again (JP-A-63-23896) or carrying out a hydrophobic chromatography treatment (JP-A-1-275600). However, the immobilized heparin treatment results in low activity recovery yield even by a single treatment, and the hydrophobic chromatography treatment has a possibility of leaving contaminant proteins, such as prealbumin, transferrin, IgG and the like, so that it is necessary that the purification step is carried out again for removing these proteins, and as a result, the activity recovering yield is reduced.

SUMMARY OF THE INVENTION

An object of the present invention is to provide a method for producing AT-III suitable for use in a medical treatment, by stably maintaining the activity of AT-III and reducing denaturation of AT-III (conformational changes, such as dimerization, polymerization, and the like) when AT-III is heated in the liquid state.

Furthermore, an object of the present invention is to provide a method for removing contaminant proteins, such as inactivated AT-III and the like, as a single step, while maintaining the activity of AT-III.

That is, the present invention relates to a method for producing AT-III, a method for purifying it, and a preparation containing it.

Specifically, these and other objects of the present invention have been attained by a method for producing AT-III from an AT-III-containing aqueous solution, comprising at least one of the following steps (a) and (b):
(a) heating the AT-III-containing aqueous solution in the presence of a stabilizing agent so that 85% or more of the activity of antithrombin-III before the heating is maintained after the heating, and that the ratio of an antithrombin-III monomer after the heating is maintained at 95% or more; and
(b) treating the AT-III-containing aqueous solution with a metal chelate resin and recovering a purified AT-III.

Furthermore, these and other objects of the present invention have been attained by a pharmaceutical composition comprising the AT-III produced according to the above process or a pharmaceutically acceptable salt thereof as an active ingredient, optionally together with a pharmaceutically acceptable carrier.

DETAILED DESCRIPTION OF THE INVENTION (I) Starting material

Examples of the AT-III-containing aqueous solution (hereinafter often referred to as the "AT-III aqueous solution") include mixtures of blood plasma proteins, such as fraction (Fr.) II+III supernatant and IV obtained by Cohn's cold ethanol method and a residual fraction from the recovery of blood coagulation factor VIII from citrate-containing blood plasma; however, the starting material is not particularly limited to blood plasma origin, so that a solution containing AT-III obtained, for example, by a genetic engineering or the like technique can be also introduced into the AT-III purification method.

Specific purification methods for obtaining AT-III from blood or plasma are disclosed in U.S. Pat. No. 3,842,061 (JP-A-48-35017), U.S. Pat. No. 4,340,589 (JP-A-54-95715), EP-A-339919 (JP-A-1-275600), and EP-A-551084. For example, a method is used in which a low temperature ethanol fraction IV-1, IV or II+III of a supernatant fluid obtained by removing cryoprecipitate from blood plasma is further purified through, e.g., heparin affinity chromatography.

In addition, AT-III prepared by a cell culture method [for example, EP-A-53165 (JP-W-57-500768) [the term "JP-W" as used herein means an "unexamined published Japanese international patent application"], or a genetic engineering technique [for example, EP-A-90505 (JP-A-58-162529)] can also be used.

(II) Heat treatment

According to the heat treatment of the present invention, the AT-III aqueous solution is subjected to a heat treatment at an appropriate temperature for an appropriate period of time which are sufficient for inactivating contaminant virus potentially contained therein. Specifically, the treatment may be carried out at 50 to 70° C., preferably about 60° C., for 10 minutes to 20 hours, preferably about 10 hours. The pH of the solution is 5 to 10, preferably 6.5 to 9.0, and is more preferably adjusted with an appropriate buffer. The AT-III aqueous solution contains AT-III in a ratio of from 10 to 500 units/ml, preferably from 10 to 200 units/ml, and more preferably from 25 to 100 units/ml. According to the present invention, "1 unit" of AT-III means an AT-III activity corresponding to the amount of AT-III contained in 1 ml of normal human plasma. The AT-III activity can be measured, for example, using an AT-III activity measuring kit using a synthetic substrate (Test Team AT-III-2-Kit, manufactured by Daiichi Pure Chemicals Co., Ltd.).

The heat treatment is carried out in such a manner that the total activity of AT-III after the heat treatment is maintained at 85% or more, preferably 95% or more, of the total activity before the heat treatment, and the ratio of an AT-III monomer in the total amount of the AT-III aqueous solution is maintained at 95% or more, preferably 99% or more.

The ratio of an AT-III monomer can be measured, for example, by high performance liquid chromatography (HPLC) using G 3,000 $SW_{XL}$ column (manufactured by Tosoh Corp.) previously equilibrated with 0.3 M sodium chloride-0.05 M phosphate buffer (pH 7.0).

In order to satisfy such conditions of residual activity and monomer ratio, the heat treatment may be carried out in the presence of a stabilizing agent described below.

(III) Stabilizing agent

The stabilizing agent for the heat treatment in the present invention is preferably selected from organic acids or salts thereof, saccharides, and sodium chloride.

The organic acid for use in the present invention is analiphatic or aromatic, saturated or unsaturated monobasic acid (monocarboxylic acid), dibasic acid (dicarboxylic acid) or tribasic acid (tricarboxylic acid). Preferably, the acid has 2 to 10 carbon atoms, more preferably 2 to 6 carbon atoms. Examples of the monobasic acid include monobasic amino acids (e.g., glycine, alanine, valine, leucine, isoleucine). Examples of the dibasic acid include saturated aliphatic dicarboxylic acids (e.g., oxalic acid, malonic acid, succinic acid, glutaric acid, adipic acid), saturated aliphatic dicarboxylic acids (e.g., maleic acid, fumaric acid), aromatic dicarboxylic acids (e.g., phthalic acid), dibasic amino acids (e.g., aspartic acid, glutamic acid), dibasic hydroxy acids (e.g., malic acid, tartaric acid). Examples of the tribasic acid include tribasic hydroxy acids (e.g., citric acid). Of these, malic acid, tartaric acid, maleic acid, aspartic acid and citric acid are preferred, and malic acid and citric acid are more preferred.

In addition, such an organic acid may be used in the form of a salt. Examples of the organic acid salts include alkali metal salts (e.g., sodium salts, potassium salts), alkaline earth metal salts (e.g., calcium salts), and organic salts (e.g., ammonium salts). Sodium salts and calcium salts are preferred. The preferred organic acid salts for use in the present invention are sodium malate and sodium citrate, and sodium citrate is most preferred.

The organic acids or salts thereof are added within the range of preferably 3 to 20 w/v %, more preferably 3 to 10 w/v %, and most preferably from 3 to 5 w/v %. If the amount is smaller than 3 w/v %, the stabilizing effect is reduced.

The organic acid or a salt thereof and a saccharide are essentially used. Sodium chloride may not be used alone. The addition of saccharides or sodium chloride reduces the amount of the organic acid to be added and inhibits denaturation (dimerization and polymerization of AT-III) which causes inactivation of the AT-III activity. Examples of the saccharides include monosaccharides, disaccharides, sugar alcohols, and amino sugars. Examples of the monosaccharides include glucose, fructose, galactose, mannose, arabinose, and inositol. Examples of disaccharides include saccharose, lactose, and maltose. Examples of the sugar alcohols include mannitol, sorbitol, and xylitol. Examples of the amino sugars include glucosamine and N-acetyl-D-glucosamine which is an amino sugar derivative. Of these, preferred are saccharose, lactose, sorbitol, inositol, maltose, N-acetyl-D-glucosamine and mannitol.

The saccharides are added within the range of preferably 10 to 60 w/v %, more preferably 20 to 50 w/v %, and most preferably 20 to 30 w/v %. If the amount is smaller than 10 w/v %, the stabilizing effect is reduced; and if the amount is larger than 60 w/v %, it is also disadvantageous, because although increased stabilization can be obtained, contaminant viruses would also be stabilized.

Sodium chloride is added within the range of preferably 0.5 to 3.0 M, more preferably 1.0 to 2.5 M, and most preferably 1.5 to 2.0 M. If the amount is smaller than 0.5 M, the stabilizing effect is reduced; and the amount larger than 3.0 M is also disadvantageous, because although increased stabilization can be obtained, the solubility of AT-III would be reduced.

However, according to the present invention, amounts of the stabilizing agents to be added are not particularly limited to the above ranges, as long as they satisfy the conditions that the total activity of AT-III after the heat treatment is maintained at 85% or more of the total activity before the heat treatment, and the ratio of an AT-III monomer after the heat treatment is maintained at 95% or more.

(IV) Purification

The AT-III purification method of the present invention comprises treating AT-III with a metal chelate resin within an AT-III purification step. More specifically, the method comprises, in purifying AT-III from an AT-III-containing aqueous solution, allowing the AT-III-aqueous solution to contact with a metal chelate resin and recovering the non-adsorbed fraction.

The AT-III aqueous solution may have a protein concentration of about 0.1 to 5 w/v %. Also, it is preferred to use an AT-III aqueous solution which has been purified to a certain degree, preferably an AT-III aqueous solution prepurified using the above-described heparin-immobilized carrier. In addition, it is preferred to carry out a virus inactivation treatment of the AT-III aqueous solution by a heat treatment (50 to 70° C., 5 to 30 hours), preferably by the above heat treatment, before subjecting the solution to the metal chelate resin treatment of the present invention.

Also, when the AT-III aqueous solution contains a chelating agent such as citric acid or the like, it is preferred to use the AT-III aqueous solution after removing the chelating agent by dialysis treatment or the like in order to prevent elution of metal ions from the metal chelate resin.

The metal chelate resin for use in the present invention is obtained by chelate-bonding a metal ion to a chelate resin, and includes a commercially available chelate resin (e.g., iminodiacetic acid type). Specific examples include Chelating-Sepharose F.F. (manufactured by Pharmacia) and AF-Chelate Toyopearl 650M (manufactured by Tosoh Corp.).

The metal ion to be bound to the chelate resin is not particularly limited, provided that it is a metal ion effective for separating AT-III. Examples include a copper ion, a nickel ion, and a cobalt ion, and a copper ion is particularly preferred in view of purification efficiency.

The method of the present invention is carried out by allowing the AT-III aqueous solution to contact with the metal chelate resin. Such a contact can be effected by either a column method or a batch method; however, it is preferred to use a column method in view of purification degree and purification efficiency.

With regard to the contacting conditions, the reaction may be carried out at pH from 6 to less than 8, preferably 6.5 to 7.7, and at a salt concentration of 0 to 1 M, preferably 0.05 to 0.5 M. Preferred solvent includes a 0.1 M phosphate buffer (pH 7.0 to 7.5) containing 0.05 to 0.5 M sodium chloride, but sodium chloride is not essential. In order to improve separation efficiency between the metal chelate resin and AT-III, an antagonist, such as glycine, imidazole, may be added to the buffer, and, it is preferred to add the antagonist in an amount of 20 mM or less.

When the purification method of the present invention is carried out by a column method, the AT-III aqueous solution adjusted to the above-described conditions is applied to a metal chelate resin column equilibrated under the same conditions (the same buffer is used as the development solution maintained at 2° C. to room temperature), and then the non-adsorbed fraction is recovered. The amount of the metal chelate resin used can be adjusted depending on the impurity content, AT-III content and the like in the AT-III-containing aqueous solution; however, generally, about 1 ml of the metal chelate resin is used per 4 ml of the AT-III aqueous solution. The elution rate from the column can be controlled depending on the packed amount of the metal chelate resin and the column size and the like.

When the purification method of the present invention is carried out by a batch method, the AT-III aqueous solution adjusted to the above-described conditions is allowed to contact with the metal chelate resin equilibrated under the same conditions, at 2° C. to room temperature, and then the supernatant fluid is recovered by centrifugation. The contacting time can be adjusted depending on the impurity content, AT-III content and the like in the AT-III-containing aqueous solution, but about 10 minutes to 1 hour of contact may be generally sufficient.

Also, metal ions may be leaked from the metal chelate resin in some cases; however, the leaked metal ions can be removed easily, for example, by a method in which they are treated with a chelate resin or an ion exchanger to which metal ions are not bound or a method in which a chelating agent such as EDTA is added and then dialysis is carried out.

The AT-III thus purified by the purification method of the present invention is substantially free from impurity proteins, denatured AT-III, AT-III polymers and the like, so that highly purified AT-III can be obtained by one step.

Moreover, the AT-III thus purified by the purification method of the present invention may be further purified according to objectives by a conventional purification means, such as an anion exchanger treatment or a treatment with an insoluble carrier having hydrophobic groups as its ligands.

(V) Posttreatment

The AT-III thus subjected to the virus inactivation treatment and/or purified by the method according to the present invention is made into a pharmaceutical preparation in accordance with usually used formulation methods. Examples of the pharmaceutical preparation include aqueous solutions, suspensions and freeze-dried preparations which can be prepared in the usual way by optionally mixing with pharmaceutically acceptable carriers and additives (e.g., diluents, tonicity agents, surface active agents). Administration of the AT-III preparation can be carried out in accordance with the conventional prescription of AT-III injections or intravenous drip injections, for example by carrying out slow intravenous injection or drip injection of a liquid preparation.

The AT-III produced and/or purified by the present invention is useful for treating thrombus forming tendency caused by congenital AT-III deficiency and disseminated intravascular coagulation syndrome (DIC) which accompanies reduction of AT-III in the body.

In general, AT-III is administered at a ratio of 1,000 to 3,000 units per day (or 20 to 60 units/kg body weight), although such a dosage may be optionally changed depending on the conditions such as age, body weight, symptoms and the like. Also, when the preparation according to the present invention is used as an emergency treatment for obstetric or surgical DIC, it is preferred to administer it at a dose of 40 to 60 units/kg body weight once a day. It is preferred that osmotic pressure of the liquid preparation is the same as or close to the physiological condition of human and animal patients.

(VI) Effect of the invention

When AT-III is heated in the liquid state in order to inactivate viruses in accordance with this invention, activity of AT-III can be maintained stably and denaturation of AT-III (conformational changes such as dimerization, polymerization and the like) can be reduced, so that AT-III having markedly high safety and availability from a medical point of view can be produced.

Furthermore, according to the purification method of the present invention, impurity proteins contained in the AT-III aqueous solution and denatured AT-III and polymers formed by the heat treatment can be removed effectively, so that AT-III having high safety can be obtained. In addition, since the purification treatment step is simple and suitable for a large scale production, it is markedly useful as an industrial production method.

Since the pharmaceutical preparations of the present invention contain AT-III purified by the above-described method, pharmaceutical AT-III preparations having excellent safety can be provided.

The present invention is described further in detail with reference to the following examples which, however, do not restrict the invention in any way. The materials and methods used in the following experiments are as follows.

Materials and Methods:

(1) AT-III Material

The starting material used herein was prepared by concentrating a solution derived from Cohn's Fr. II+III supernatant fluid or Fr. IV, which has been purified using a heparin-immobilized column, and subjecting the solution to a virus inactivation treatment by heating it at 60° C. and at pH 7.8 for 10 hours in the presence of 5% sodium citrate, 2 M NaCl and 30% sorbitol.

(2) Chromatography carrier for purification use

Chelating-Sepharose F.F. (manufactured by Pharmacia) or AF-Chelate Toyopearl 650M (manufactured by Tosoh Corp.) was used as the chelate chromatography carrier.

(3) Measurement of AT-III activity and calculation of residual ratio

The measurement was carried out by a synthetic substrate method using S-2238. The S-2238 and reaction termination solution used were those attached to Test Team AT-III-2-Kit (Daiichi Pure Chemicals Co., Ltd.). One vial (20 mg) of S-2238 was dissolved in 21 ml of water. Thrombin solution (1.2 U/ml) and standard AT-III solution (1 U/ml) manufactured by The Green Cross Corporation were dispensed in portions and stored at −40° C. to be thawed out again when used. A 50 μl portion of each sample to be tested which had been adjusted to 1 to 10 mU/ml with a solution containing 40 mM Tris, 60 mM EDTA, 0.14 M NaCl, 0.2% HSA (human serum albumin) and 2.4 U/ml of heparin, pH 8.4, was mixed with 100 μl of the thrombin solution and incubated at 37° C. for 5 minutes. Next, this was mixed with 100 μl of the substrate solution and incubated exactly for 5 minutes and then the reaction was terminated by adding 1,000 μl of the reaction termination solution. Absorbance of the solution was measured at 405 nm, and AT-III activity of the sample was calculated from a standard straight line which has been prepared using the standard AT-III solution.

Residual ratio of the AT-III activity was calculated by the percentage of the total AT-III activity [U/ml×liquid volume (ml)] of each AT-III sample after the heat treatment to the total AT-III activity before the heat treatment, with the results shown in Table 1.

(4) AT-III specific activity

The amount of protein in each sample to be tested was calculated by measuring its absorbance at $A_{280\ nm}$ (hereinafter referred to as "$A_{280}$"). Specific activity ($U/A_{280}$) of each sample was obtained by dividing the AT-III activity obtained above by the amount of protein, with the results shown in Table 1.

(5) Gel filtration HPLC analysis

This analysis was carried out by System Gold (manufactured by Beckman) equipped with G3000 $SW_{XL}$ (φ 7.8 mm×30 cm, manufactured by Tosoh) column, using a solution containing 50 mM sodium phosphate and 0.3 M NaCl, pH 7.0, as the developing solution. The flow rate was 0.7 ml/min, and the detection was effected at the absorbance of 280 nm in all cases.

The ratio of an AT-III monomer obtained by the HPLC analysis is shown in Table 1. Also, degree of denaturation of AT-III (conformational changes such as dimerization, polymerization and the like) can be obtained from the results of Table 1.

(6) Ouchterlony analysis

This analysis was carried out in the usual way by optionally concentrating each sample to be tested to an absorbance of about 30 at 280 nm. The antibodies used are as follows (the numbers correspond to those in FIG. 4): Anti-human ceruloplasmin (1) (Hoechst N-anti-serum ceruloplasmin); anti-human transferrin (2) (Hoechst N-anti-serum transferrin); anti-human albumin (3) (Hoechst N-anti-serum albumnin); anti-human prealbumin (4) (Hoechst N-anti-serum prealbumin); anti-human haptoglobin (5) (DAKO A030); anti-human $\alpha_2$ macroglobulin (6) (DAKO A033); anti-human $\alpha_1$ antitrypsin (7) (DAKO A012); anti-human IgA (8) (DAKO A02621); anti-human IgG (9) (DAKO A04231); anti-human IgM (10) (Hoechst anti-IgM (μ chain) rabbit serum); anti-human prothrombin (11) (DAKO A325); and anti-human fibrinogen (12) (DAKO A080).

EXAMPLE 1

A 10 kg portion of a paste of the fraction IV-1 obtained by the Cohn's low temperature ethanol fractionation method was suspended in 100 liters of physiological saline, barium sulfate was added to the suspension to a concentration of 5 w/v %, and the mixture was stirred at room temperature for 30 minutes to remove trace amount of existing prothrombin by its adsorption by barium sulfate. The supernatant fluid thus obtained was adjusted to pH 6.5, mixed with 13 w/v % of polyethylene glycol # 4,000 (average molecular weight test: 2,600 to 3,800, manufactured by Nippon Soda Co., Ltd.) and the precipitate thus obtained removed by centrifugation; and then the resulting supernatant fluid was again mixed with 30 w/v % of the polyethylene glycol # 4,000 and the thus formed precipitate was recovered by centrifugation.

The precipitate thus recovered was dissolved in about 20 liters of cold physiological saline and applied to a heparin-Sepharose (manufactured by Pharmacia) column which had been equilibrated in advance with physiological saline to adsorb AT-III on the column. The column thus prepared was washed with 0.4 M sodium chloride solution to remove impurity proteins and then 2.0 M sodium chloride solution was passed through the column to recover the eluted AT-III portion.

The AT-III aqueous solution thus obtained was mixed with the stabilizing agents shown in Table 1, adjusted to pH 7.8 and then subjected to a heat treatment at 60° C. for 10 hours. The AT-III aqueous solution thus treated was allowed to contact with a butyl type polyvinyl carrier (Butyl Toyopearl 650, manufactured by Tosoh Corp.) which had been equilibrated in advance with 20 mM sodium citrate buffer (pH 7.5) containing 3 M sodium chloride, and the same buffer was used as the development solution to recover non-adsorbed fraction. This was then dialyzed overnight against 0.5% sodium citrate buffer (pH 7.5) to obtain purified AT-III.

Activity of each of the purified AT-III samples after the heat treatment was measured to calculate its residual ratio to the activity of AT-III before the heat: treatment. The ratio of the monomer of each AT-III sample was also obtained.

TABLE 1

| Stabilizing agents | Specific activity ($U/A_{280}$) | Residual ratio (%) | HPLC (%) |
|---|---|---|---|
| Before heat treatment | 8.8 | 100 | 99.7 |
| 19 w/v % Na-Cit, 2 M NaCl pH 7.8 | 6.9 | 78.4 | 78.9 |
| 5 w/v % Na-Cit  2 M NaCl  60 w/v % Sorb. pH 7.8 | 7.5 | 84.7 | 86.4 |
| 5 w/v % Na-Cit  2 M NaCl  10 w/v % Sorb. pH 7.8 | 8.0 | 85.0 | 90.0 |
| 20 w/v % Sorb. pH 7.8 | 8.4 | 88.4 | 95.0 |
| 30 w/v % Sorb. pH 7.8 | 8.6 | 90.3 | 95.2 |

TABLE 1-continued

| Stabilizing agents | | Specific activity ($U/A_{280}$) | Residual ratio (%) | HPLC (%) |
|---|---|---|---|---|
| | 40 w/v % Sorb. pH 7.8 | 7.8 | 88.0 | 96.7 |
| | 50 w/v % Sorb. pH 7.8 | 8.1 | 92.0 | 99.3 |
| | 60 w/v % Sorb. pH 7.8 | 8.2 | 93.6 | 99.7 |
| 10 w/v % Na-Cit | 40 w/v % Sorb. pH 7.8 | 7.6 | 85.7 | 97.7 |
| | 50 w/v % Sorb. pH 7.8 | 7.7 | 87.7 | 91.9 |
| | 60 w/v % Sorb. pH 7.8 | 8.1 | 91.4 | 98.9 |
| | 2 M NaCl, 50 w/v % Sorb. pH 7.8 | 7.9 | 89.8 | 96.7 |

Residual ratio (%): percentage of the total AT-III activity after the heat treatment to the total AT-III activity before the heat treatment
HPLC analysis (%): ratio of AT-III monomer Synergistic effect was observed when sodium citrate and sodium chloride were added, so that dimerization and polymerization were able to be prevented and the stabilizing effect was observed at a low concentration of sodium citrate. In the above table, Na-Cit means sodium citrate, and Sorb. means sorbitol.

EXAMPLE 2

Purification of AT-III using Chelating-Sepharose F.F.:

To a 1.5 ml column (φ 0.9×2.3 cm) of Chelating-Sepharose F.F. was added the same bed volume (1.5 ml) of $CuSO_4 \cdot 5H_2O$ which had been dissolved in water to a concentration of 10 mg/ml to bind the metal, and then the column was washed with 2 bed volumes (3 ml) of water. Next, the column was equilibrated by passing 3 bed volumes of a solution containing 0.1 M sodium phosphate and 0.5 M NaCl, pH 8.0. Using PD-10 column (manufactured by Pharmacia), 3 ml of a heat-treated concentrated solution of AT-III ($A_{280}$=4.20) which had been exchanged by the same buffer was added to the column thus prepared, and the eluted fractions were collected at a rate to 1.5 ml/Fr (fraction). Thereafter, solutions containing 0.1 M sodium phosphate and 0.5 M NaCl adjusted to pH 7.5, 7.0 and 6.0 were added each in 3 bed volumes (4.5 ml) to the column, and the fractions eluted were collected at 1.5 ml/Fr in the same manner. Also, the chelate column used was regenerated by removing the bound metal with 2 bed volumes of 50 mM EDTA.2Na and then passing 3 bed volumes of water.

Figure 1:
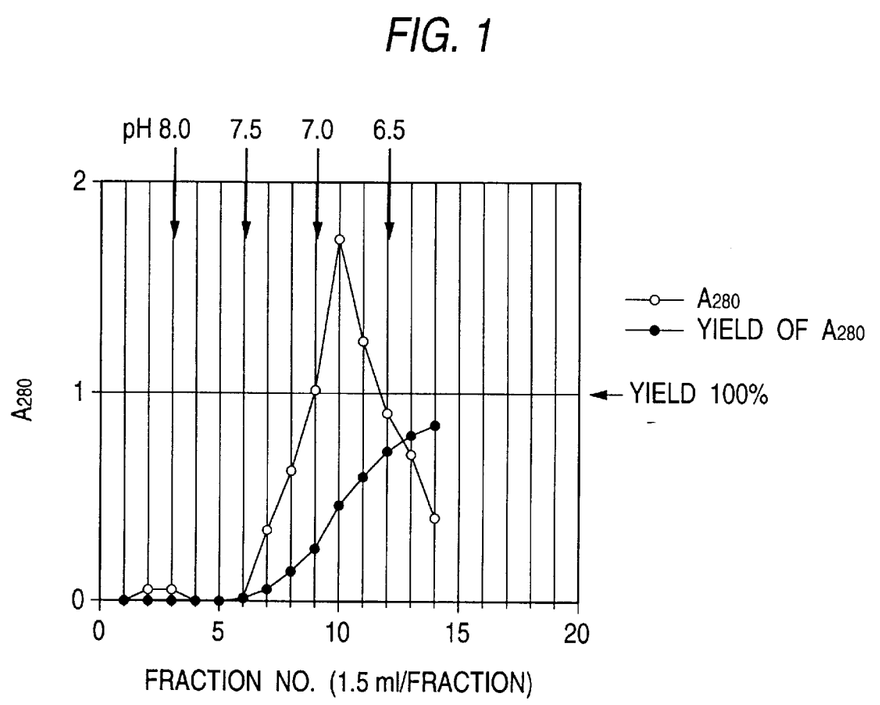
FIG. 1 is a graph showing an elution pattern of AT-III from a copper ion-bound chelate resin.

The results are shown in FIG. 1. As is evident from FIG. 1, most of the protein was adsorbed at pH 8.0 and eluted at pH 7.5 or less in the copper chelate column.

Table 2 shows results of the GPC-HPLC analysis of eluates from the copper chelate column. As shown in Table 2, purity of non-denatured (intact) AT-III was 88.0% before its addition to the copper chelate column; however, the purity in the eluted Fr from the column became 100% at all pH values tested. That is, it was found that denatured AT-III and impurity proteins can be removed markedly efficiently by passing the solution through the column at a pH value of less than 8, preferably at pH 7.5 or less, and these impurities are retained by the column even at pH 6.5

TABLE 2

| Fraction No. | 1–5 | 6 | 7 | 8 | 9 | 10 | 11 | 12 | 13 | 14 |
|---|---|---|---|---|---|---|---|---|---|---|
| pH | 8.0 | | 7.5 | | | 7.0 | | | 6.5 | |
| Intact AT-III purity (%) | — | | 100 | | | 100 | | | 100 | |

Purity of intact AT-III of the sample added to the column: 88.0%

EXAMPLE 3

Figure 2:
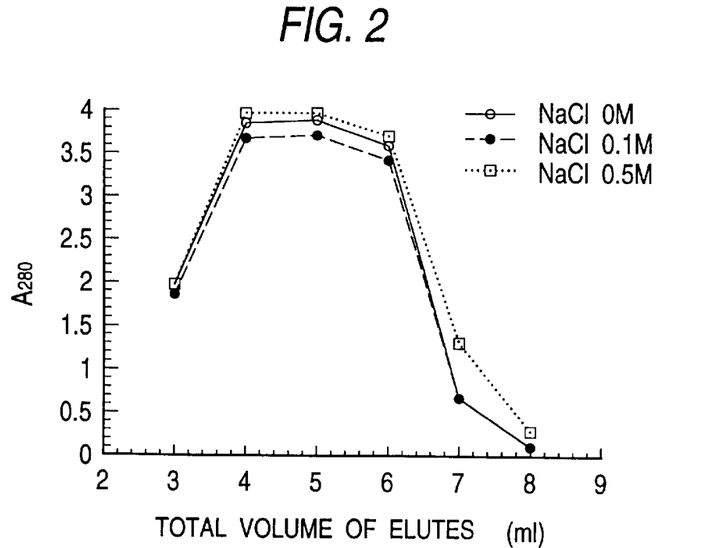
FIG. 2 is a graph showing effect of a salt concentration on the elution pattern of AT-III from a copper ion-bound chelate resin.

Effects of salt concentration:

In order to examine effects of the salt concentrations in the chromatography buffer, copper chelate chromatographic behavior of a heat-treated and concentrated AT-III solution was examined using 0.1 M sodium phosphate buffer (pH 7.5) or a buffer solution prepared by adding 0.1 M NaCl or 0.5 M NaCl to 0.1 M sodium phosphate (pH 7.5). That is, a heat-treated and concentrated AT-III solution was subjected to solvent exchange with each buffer solution by PD-10 column, its $A_{280}$ value was adjusted to about 5 and then a 5 ml portion of each solution was applied to 1 ml of a copper chelate column (φ 0.8×2 cm) which had been equilibrated with the same buffer. Initial 3 ml portion of the passed solution was pooled, and the rest was collected in 1 ml portions. Thereafter, the column was washed with respective buffer, and the eluates at the time of washing were collected in 1 ml portions. The elution pattern is shown in FIG. 2. Also, results of the GPC-HPLC measurement of intact AT-III purity in each elution fraction are shown in Table 3.

TABLE 3

| Fraction No. | Total volume of eluates (ml) | Intact AT-III purity (%) NaCl concentration (M) | | |
|---|---|---|---|---|
| | | 0 | 0.1 | 0.5 |
| 1 | 3 | 100.0 | 100.0 | 100.0 |
| 2 | 4 | 100.0 | 100.0 | 100.0 |
| 3 | 5 | 100.0 | 100.0 | 100.0 |
| 4 | 6 | 100.0 | 100.0 | 100.0 |
| 5 | 7 | 100.0 | 100.0 | 100.0 |

Purity of intact AT-III of the sample added to the column: 81.15%

As shown in FIG. 2, no significant difference was found in the elution pattern between the case containing no NaCl and the case containing 0.1 M or 0.5 M NaCl. Also, as shown in Table 3, the purity of intact AT-III in the eluates was 100.0% in all cases. In consequence, it was revealed that changes in the salt concentration of the buffer hardly exert influence upon the chromatographic behavior.

Also, effect of pH changes on the chromatographic behavior was examined using 0.1 M sodium phosphate buffer (containing 0.1 M NaCl) which was adjusted to pH 7.3, 7.5 or 7.7; however, it was revealed that changes in pH within this range hardly exert influence upon the chromatographic behavior. Also, chromatographic behavior at 4° C. and room temperature was examined using 0.1 M sodium phosphate buffer (containing 0.1 M NaCl, pH 7.5); however, it was revealed that changes in temperature within this range hardly exert influence upon the chromatographic behavior.

EXAMPLE 3
Confirmation of purification degree and evaluation of purification yield in a scale-up test:

A heat-treated and concentrated AT-III solution was subjected to buffer exchange with 0.1 M sodium phosphate containing 0.1 M NaCl, pH 7.5, by PD-10 column ($A_{280}$= 4.05) and then a 25 ml portion of the solution was applied to 5 ml of a copper chelate Toyopearl 650 M column ($\phi$ 1.5×2.8 cm) which had been equilibrated with the same buffer. A 2.5 ml portion equivalent to half the volume of the column bed was discarded and then the eluate obtained simiultaneously with the sample application and 2 column bed equivalent of washed water with the equilibration buffer were combined and pooled (32.5 ml) to be used as purified AT-III.

Figure 3:
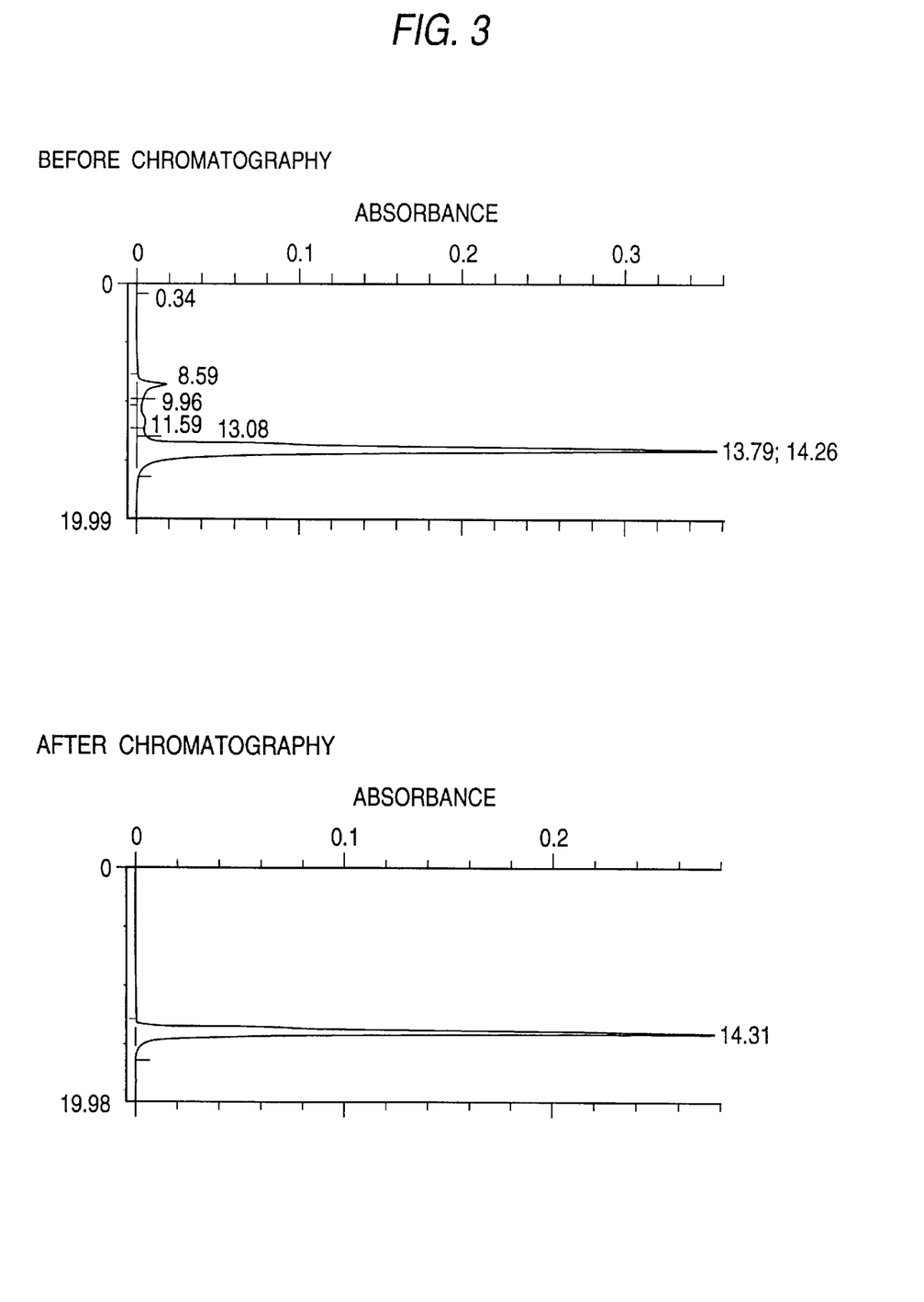
FIG. 3 is a graph showing HPLC-GPC patterns before and after purification of AT-III by a copper ion-bound chelate resin.

The $A_{280}$ values and AT-III activity recovery yields are shown in Table 4, and the GPC-HPLC patterns before and after the chromatography are shown in FIG. 3.

As shown in Table 4, good recovery yields were obtained, namely 80.3% for $A_{280}$ and 89.6% for AT-III activity. Also, as shown in FIG. 3, the column eluate of GPC-HPLC showed a single peak of intact AT-III and contained no polymers, denatured AT-III and other impurity proteins.

Figure 4:
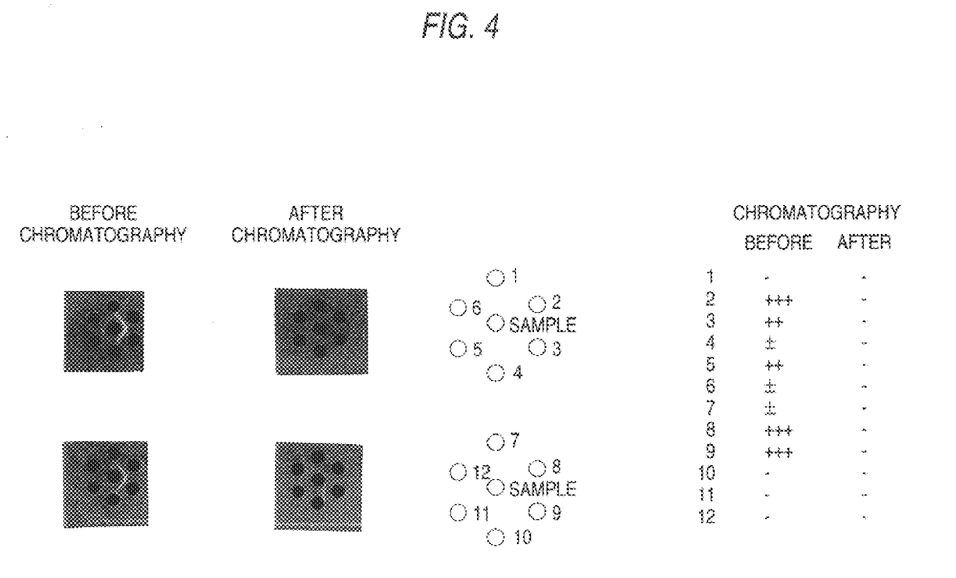
FIG. 4 is a graph showing results of impurity analysis by Ouchterlony method before and after purification of AT-III from a copper ion-bound chelate resin.

In addition, when the above sample was subjected to Ouchterlony analysis, all of the potential impurity proteins (namely ceruloplasmin, transferrin, albumin, prealbumin, haptoglobin, $\alpha_2$ macroglobulin, $\alpha_1$ antitrypsin, IgA, IgG, IgM, prothrombin and fibrinogen) were not detected (see FIG. 4).

Thus, it was revealed that all of the impurity proteins, polymers and denatured AT-III can be removed by the copper chelate Toyopearl 650M chromatography at pH 7.5.

TABLE 4

| | | $A_{280}$ | | | AT-III activity | | |
|---|---|---|---|---|---|---|---|
| Step | Vol (ml) | $A_{280}$ | $A_{280}$ × Vol | Yield (%) | U/ml | Total Activity | U/$A_{280}$ | Yield (%) |
| Column Added | 25 | 4.05 | 101.3 | 80.3 | 29.9 | 748 | 7.38 | 89.6 |
| Column Passed | 32.5 | 2.50 | 81.3 | | 20.6 | 670 | 8.26 | |

EXAMPLE 5
Elimination of leaked copper from copper chelate resin column

In copper chelate column chromatography, it is known that the copper bound to the column is generally leaked in a small amount with the adsorption of protein. As a method for the elimination of leaked copper, a technique has been recommended in which a small metal-non-bound chelate resin (i.e., the chelate can bind metal but the metal is absent) column is connected to a metal chelate resin column. In consequence, effect of this method to eliminate leaked copper was examined as follows. A 20 ml portion of Fr. II+III supernatant-derived heat-treated and concentrated AT-III solution ($A_{280}$=4.96), dissolved in 0.1 M sodium phosphate buffer containing 0.1 M NaCl, pH 7.5, was added to a copper chelate Toyopearl column ($\phi$ 1.5×2.8 cm, 5 ml) which has been equilibrated with the same buffer, and the non-adsorbed fractions were pooled (27.5 ml, $A_{280}$=3.18). A 23.5 ml portion of this was added to a metal-non-added chelate Toyopearl 650M column ($\phi$ 0.8×2.0 cm, 1 ml) which had been equilibrated in the same manner, and the non-adsorbed fractions were pooled (25 ml, $A_{280}$=2.63). Results of the measurement of the copper content in each step are shown in Table 5.

TABLE 5

| Step | Copper content (ppb) |
|---|---|
| Copper chelate column added | 320 |
| Copper chelate column passed | 10,300 |
| Metal-non-bound chelate column passed | 15 |
| Negative control (chromato buffer) | 13 |

As shown in Table 5, although 10,300 ppb of leaked copper was found in the copper chelate column pass, it was found that the leaked copper could fully be eliminated by passing the solution through the metal-non-bound chelate Toyopearl 650M column, because the leak was reduced to 15 ppb which was close to the control level (13 ppb).

Figure 5:
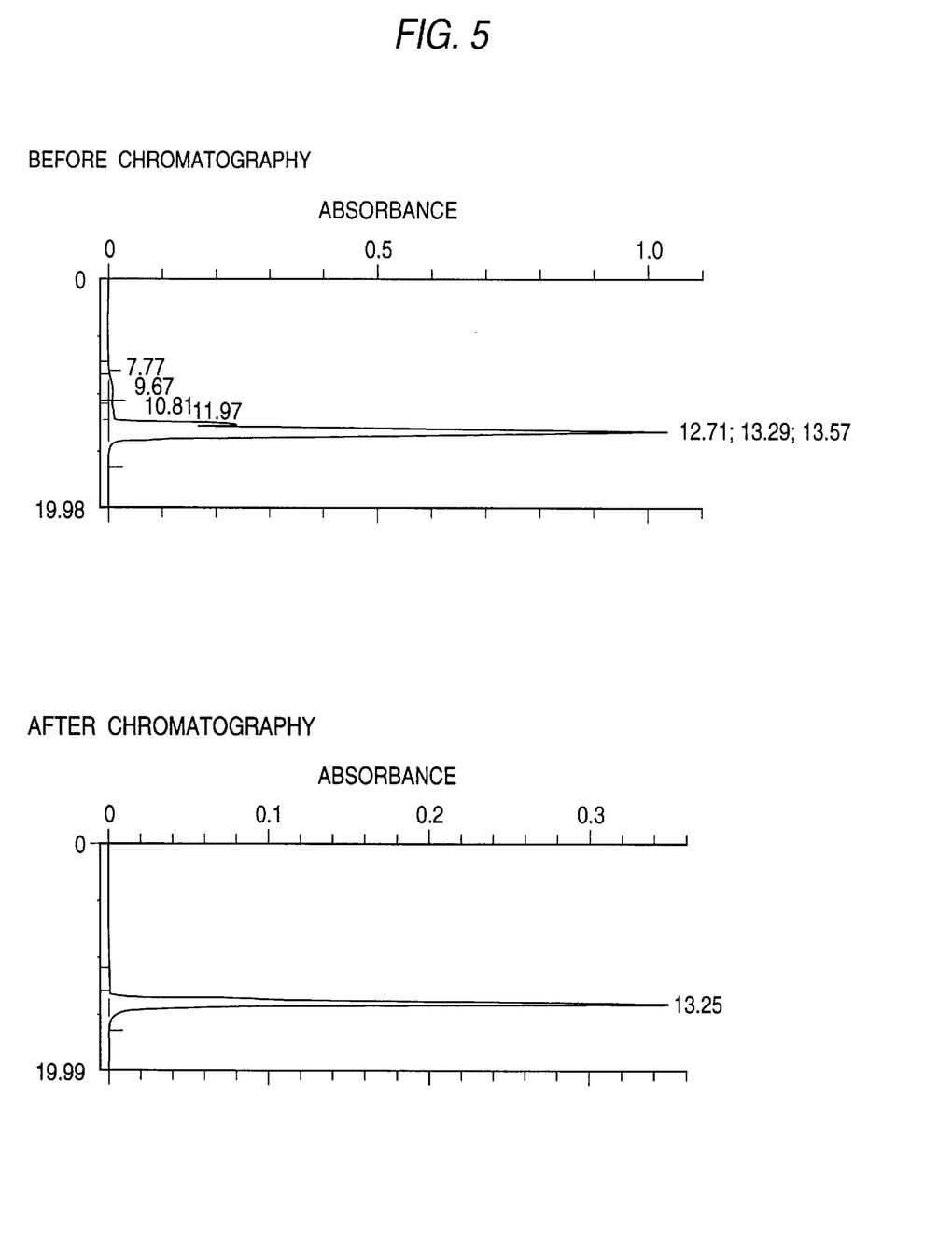
FIG. 5 is a graph showing HPLC-GPC patterns before and after purification of AT-III by copper ion-bound chelate resin+metal-non-bound chelate resin.

GPC-HPLC patterns of the starting material and the eluate of metal-non-added chelate column are shown in FIG. 5. As shown in FIG. 5, it was found that even a material derived from Fr. II+III supernatant was able to be purified by a copper chelate column, because clear peaks were not found other than that of intact AT-III. Its purity calculated from the peak area was 99.9%.

EXAMPLE 6
Purification yield by connected columns of copper chelate and metal-non-bound Toyopearl:

Taking efficiency improvement and automation of the chromatography step into consideration, an examination was made on connected columns of copper chelate and metal-non-added chelate. A heat-treated and concentrated solution of AT-III derived from Fr. II+III supernatant or Fr. IV was dialyzed 1,600 times against 0.1 M sodium phosphate buffer containing 0.1 M NaCl, pH 7.5, and again dialyzed 100 times against the same buffer (160,000 times dialysis in total) by concentration and dilution using Centriprep-30 (manufactured by Amicon) (Fr. IV: $A_{280}$=5.23, Fr. II+III supernatant: $A_{280}$=5.50). The dialysis multiple was increased by Centriprep-30, because leakage of copper becomes large by the 1,600 times dialysis due to residual citric acid. A 20 ml portion of each of these solutions was applied to serially connected columns of 5 ml ($\phi$ 1.5×2.8 cm) copper chelate Toyopearl and 1 ml ($\phi$ 0.8×2.0 cm) metal-non-bound chelate Toyopearl, which have been equilibrated with the same buffer. Of the solution eluted when the sample was applied, half the volume of the total column capacity was discarded, and the fractions eluted thereafter were pooled by combining them with 10 ml of washed fractions which corresponds to 2 bed volumes of the copper chelate column.

As is evident from the purification yields shown in Table 6, both of the materials derived from Fr. II+III supernatant and Fr. IV showed a good activity recovery yield of 90% or more. Also, the specific activity was around 10 U/$A_{280}$ which was equivalent to those of the pharmaceutical preparations in use.

TABLE 6

| Origin of Material | Step | Liquid Amount (ml) | $A_{280}$ | Total $A_{280}$ | Yield (%) | AT-III Activity U/ml | Total Activity | Yield (%) | Specific Activity $(U/A_{280})$ |
|---|---|---|---|---|---|---|---|---|---|
| II + III Supernatant | Column added | 20.0 | 5.50 | 110 | 100 | 49.0 | 981 | 100 | 8.9 |
|  | Column passed | 27.0 | 3.22 | 86.9 | 79.0 | 33.9 | 914 | 93.2 | 10.5 |
| IV | Column added | 20.0 | 5.23 | 105 | 100 | 40.9 | 818 | 100 | 7.8 |
|  | Column passed | 26.0 | 2.92 | 75.9 | 72.3 | 29.1 | 757 | 92.5 | 10.0 |

EXAMPLE 7
Preparation of AT-III pharmaceutical preparation:

The purified AT-III obtained in Example 5 was desalted, concentrated and filtered through a BMM (Bemberg Microporous Membrane) membrane (manufactured by Asahi Chemical Industry, Co., Ltd.). Fifty units/ml of the thus prepared AT-III sample was mixed with 2 w/v % of mannitol, 0.52 w/v % of sodium citrate and 0.5 w/v % of sodium chloride, and the mixture was adjusted to pH 7.2 to 7.5 with 1 N sodium hydroxide, sterilized by filtration through a sterilized Millipore filter, dispensed in 500 unit portions and then freeze-dried to obtain a freeze-dried pharmaceutical preparation.

While the invention has been described in detail and with reference to specific embodiments thereof, it will be apparent to one skilled in the art that various changes and modifications can be made therein without departing from the spirit and scope thereof.

This application is based on Japanese application Nos. Hei 8-309281 filed on Nov. 20, 1996 and Hei 9-163426 filed on Jun. 4, 1997, the entire contents of which are incorporated hereinto by reference.

What is claimed is:

1. A method for purifying antithrombin-III from an antithrombin-III-containing aqueous solution, comprising the following step:
    (a) heating the antithrombin-III-containing aqueous solution in the presence of, as a stabilizing agent, an organic acid or a salt thereof and a saccharide, optionally together with sodium chloride so that 85% or more of the activity of antithrombin-III before the heating is maintained after the heating, and that the ratio of an antithrombin-III monomer after the heating is maintained at 95% or more.

2. The method according to claim 1, wherein the organic acid or a salt thereof is selected from the group consisting of glycine, alanine, valine, leucine, isoleucine, oxalic acid, malonic acid, succinic acid, glutaric acid, adipic acid, maleic acid, fumaric acid, phthalic acid, aspartic acid, glutamic acid, malic acid, tartaric acid, citric acid and salts thereof.

3. The method according to claim 1, wherein the organic acid or a salt thereof is sodium citrate.

4. The method according to claim 1, wherein the saccharide is selected from the group consisting of glucose, fructose, galactose, mannose, arabinose, inositol, saccharose, lactose, maltose, mannitol, sorbitol, xylitol, glucosamine and N-acetyl-D-glucosamine.

5. The method according to claim 1, wherein the saccharide is sorbitol.

6. The method according to claim 1, wherein the organic acid or a salt thereof is contained in an amount of 3 to 20 w/v % in the solution.

7. The method according to claim 1, wherein the saccharide is contained in an amount of 10 to 60 w/v % in the solution.

8. The method according to claim 1, wherein the sodium chloride is contained in an amount of 0.5 to 3.0 mol/l in the solution.

9. The method according to claim 1, wherein the metal ion of the metal chelate resin is selected from the group consisting of a copper ion, a nickel ion and a cobalt ion.

10. The method according to claim 1, wherein the metal ion of the metal chelate resin is a copper ion.

11. The method according to claim 1, wherein the antithrombin-III-containing aqueous solution is subjected to a heat treatment before the step (b).

12. The method according to claim 12, wherein the heat treatment is carried out by heating the antithrombin-III-containing aqueous solution in the presence of, as a stabilizing agent, an organic acid or a salt thereof and a saccharide, optionally together with sodium chloride so that 85% or more of the activity of antithrombin-III before the heating is maintained after the heating, and that the ratio of an antithrombin-III monomer after the heating is maintained at 95% or more.

13. The method according to claim 12, wherein the antithrombin-III-containing aqueous solution is subjected to a dialysis treatment between the heat treatment and the step (a).

14. The method according to claim 1, wherein the heating is carried out at 50 to 70° C. for 10 minutes to 20 hours.

15. The method according to claim 1, wherein 95% or more of the activity of antithrombin-III before the heating is maintained after the heating.

16. The method according to claim 1, wherein the ratio of an antithrombin-III monomer after the heating is maintained at 99% or more.

17. The method according to claim 1, wherein the antithrombin-III-containing aqueous solution has a protein concentration of 0.1 to 5 w/v %.

18. A method for purifying antithrombin-III from an antithrombin-III-containing aqueous solution, comprising the following step:
    (a) contacting the antithrombin-III-containing aqueous solution with a metal chelate resin and recovering a purified antithrombin-III.

19. The method according to claim 18, wherein the antithrombin-III-containing aqueous solution has a protein concentration of 0.1 to 5 w/v %.

* * * * *